(12) United States Patent
Stagg et al.

(10) Patent No.: US 9,646,478 B2
(45) Date of Patent: May 9, 2017

(54) FIELD REPLACEABLE DESICCANT CARTRIDGE AND DEVICE, METHOD AND SYSTEM THEREFOR

(71) Applicant: SYMBOL TECHNOLOGIES, LLC, Lincolnshire, IL (US)

(72) Inventors: Adrian J. Stagg, Belfountain, CA (US); Gregory John Evans, Merrickville, CA (US)

(73) Assignee: Symbol Technologies, LLC, Holtsville, NY (US)

( * ) Notice: Subject to any disclaimer, the term of this patent is extended or adjusted under 35 U.S.C. 154(b) by 0 days.

(21) Appl. No.: 15/334,881

(22) Filed: Oct. 26, 2016

(65) Prior Publication Data

US 2017/0046940 A1   Feb. 16, 2017

Related U.S. Application Data

(62) Division of application No. 14/562,857, filed on Dec. 8, 2014, now Pat. No. 9,506,887.

(51) Int. Cl.
| | |
|---|---|
| *B01D 53/02* | (2006.01) |
| *G08B 21/20* | (2006.01) |
| *G01N 27/12* | (2006.01) |
| *H05K 5/02* | (2006.01) |
| *G08B 21/18* | (2006.01) |
| *G08B 5/22* | (2006.01) |

(52) U.S. Cl.
CPC ........... *G08B 21/20* (2013.01); *G01N 27/121* (2013.01); *G08B 5/22* (2013.01); *G08B 21/182* (2013.01); *H05K 5/0213* (2013.01); *H05K 5/0217* (2013.01); *H05K 5/0247* (2013.01)

(58) Field of Classification Search
CPC ...... G01N 27/121; H04M 1/02; H05K 5/0213
See application file for complete search history.

(56) References Cited

U.S. PATENT DOCUMENTS

| | | | | |
|---|---|---|---|---|
| 3,261,145 A | * | 7/1966 | Paulson ................. | B01D 53/08 95/111 |
| 3,846,730 A | | 11/1974 | Hamilton | |

(Continued)

FOREIGN PATENT DOCUMENTS

| | | |
|---|---|---|
| JP | 8295370 A2 | 11/1996 |
| WO | 2013093942 A2 | 6/2013 |

*Primary Examiner* — Christopher P Jones

(57) ABSTRACT

A field replaceable desiccant cartridge and device, method and system there for is provided. The cartridge comprises: a housing comprising an insertion end configured to removabley mate with an aperture of a device, the insertion end configured to generally prevent moisture from entering the device when mated; a desiccant located in the housing; a circuit located within the housing, the circuit in contact with the desiccant, the circuit configured to change resistance as the desiccant changes in moisture content; one or more electrodes located at an exterior of the insertion end, the one or more electrodes in contact with the circuit; and, one or more holes through the insertion end, configured to expose the desiccant to an exterior of the housing so that the desiccant can absorb moisture there from. Devices configured with the cartridge can report moisture levels to a server, which can track problems associated with moisture in the devices.

3 Claims, 13 Drawing Sheets

(56) References Cited

U.S. PATENT DOCUMENTS

| | | | |
|---|---|---|---|
| 4,546,442 A * | 10/1985 | Tinker | B01D 53/0454 700/266 |
| 5,123,277 A * | 6/1992 | Gray | B01D 53/0454 34/80 |
| 5,603,892 A | 2/1997 | Grilletto et al. | |
| 7,195,177 B2 | 3/2007 | Haws et al. | |
| 7,922,973 B2 | 4/2011 | Yamakawa | |
| 2005/0252375 A1 * | 11/2005 | Iles | F02C 7/27 95/148 |
| 2006/0065123 A1 | 3/2006 | Evans | |
| 2008/0103722 A1 | 5/2008 | Aldern et al. | |
| 2008/0110337 A1 * | 5/2008 | Hoffman | B01D 53/261 95/3 |
| 2011/0016902 A1 * | 1/2011 | Eisenhour | B60H 3/024 62/271 |
| 2014/0076048 A1 | 3/2014 | Gryska et al. | |
| 2014/0265049 A1 | 9/2014 | Burris et al. | |
| 2015/0346128 A1 * | 12/2015 | Klein | G01N 27/048 95/10 |

* cited by examiner

FIELD REPLACEABLE DESICCANT CARTRIDGE AND DEVICE, METHOD AND SYSTEM THEREFOR

BACKGROUND OF THE INVENTION

When an ingress protection ("IP") sealed enclosure rapidly transitions from a warm humid environment to a cold, low humidity environment, the moisture in the air volume within the enclosure will condense on the inside surfaces of the enclosure, as these surfaces rapidly cool. This causes problems for a handheld computer used in such situations, which includes windows which need to be free from condensation for a scanner, imager, camera or display to be useable. While this problem has been solved in the past by the use of desiccant packs within the housing, which are used to remove the moisture from the internal air volume, therefore reducing the amount of moisture available to condense on the windows, there are numerous problems with such desiccant packs. Even an IP sealed housing exchanges a small amount of air with the ambient environment by a number of means, which will introduce more moisture into the internal volume, eventually saturating the desiccant pack. For example, once the desiccant pack is saturated, this is detected by the fact that the windows in the housing start to "Fog up" when the handheld transitions from warm to cold environments, which is inconvenient and can lead to failures of the device in the field. While humidity detectors can be used to detect saturated desiccant packs, this can lead to significant product bill of material ("BOM") cost and complexity increases in design and manufacturing for the handheld. In addition, once the desiccant pack is saturated, the handheld needs to be serviced, to replace the desiccant pack, which means that the handheld needs to be taken out of service. Also, careful handling of the replacement desiccant pack is required during the service procedure, because if the desiccant pack is exposed to the ambient environment for too long, its useful life may be significantly reduced as it absorbs moisture from the ambient environment.

Furthermore, when an IP sealed enclosure is dropped or otherwise abused, the integrity of the seal can become compromised. When the IP seal is compromised, a range of equipment failures can occur, as the ambient environment leaks into the enclosure. A compromised IP seal can be detected indirectly, when the equipment is in the field, as the equipment fails due to the ingress of the ambient environment. While it is possible to detect a compromised IP seal by performing a vacuum test on the enclosure, to detect leaks in the IP seal, this requires costly equipment which is not commonly available at customer sites.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
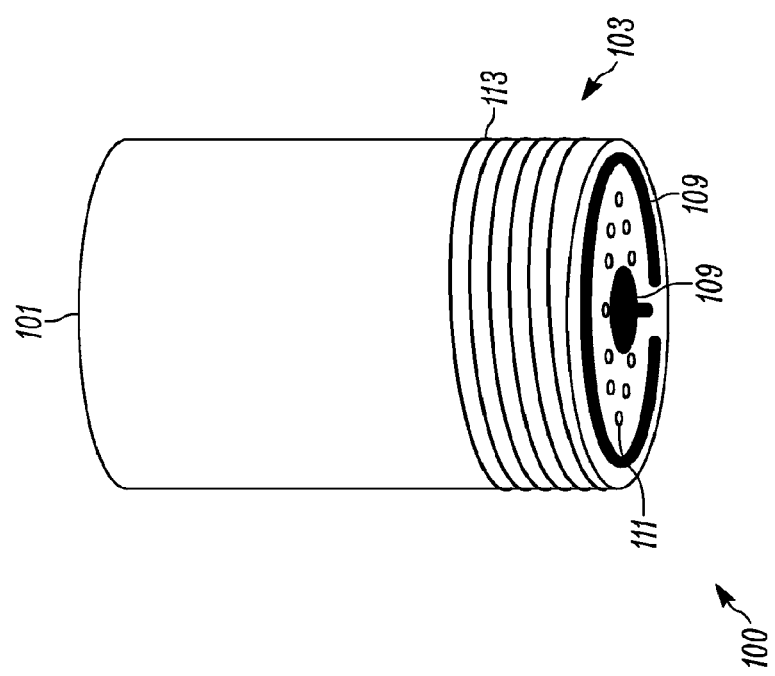
FIG. 1 is a perspective view of a field replaceable desiccant cartridge, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

An aspect of the specification provides a field replaceable desiccant cartridge comprising: a housing comprising an insertion end configured to removabley mate with an aperture of a device, the insertion end configured to generally prevent moisture from entering the device when mated; a desiccant located in the housing; a circuit located within the housing, the circuit in contact with the desiccant, the circuit configured to change resistance as the desiccant changes in moisture content; one or more electrodes located at an exterior of the insertion end, the one or more electrodes in contact with the circuit; and, one or more holes through the insertion end, configured to expose the desiccant to an exterior of the housing so that the desiccant can absorb moisture there from.

Another aspect of the specification provides a device comprising: a chassis having an aperture; a field replaceable desiccant cartridge comprising: a housing comprising an insertion end configured to removabley mate with the aperture, the insertion end configured to generally prevent moisture from entering the device when mated; a desiccant located in the housing; a circuit located within the housing, the circuit in contact with the desiccant, the circuit configured to change resistance as the desiccant changes in moisture content; one or more electrodes located at an exterior of the insertion end, the one or more electrodes in contact with the circuit; and, one or more holes through the insertion end, configured to expose the desiccant to an exterior of the housing, and an interior of the chassis of the device when mated thereto, so that the desiccant can absorb moisture there from; an ohmmeter circuit configured to measure a resistance of the circuit of the field replaceable desiccant cartridge, the ohmmeter circuit comprising one or more respective electrodes configured to contact the one or more electrodes of the field replaceable desiccant cartridge when mated thereto; and, a processor in communication with the ohmmeter circuit, the processor configured to control the ohmmeter circuit to measure the resistance of the circuit of the field replaceable desiccant cartridge.

A further of aspect of the specification provides a server comprising: a processor and a communication interface; the processor configured to: receive, using the communication interface, from a plurality of devices, respective data indicating moisture content in a respective desiccant cartridge of each of the plurality of devices, and one or more indications of respective transitions between a warm environment and a cold environment; determine respective indications of normalized rates of change of moisture content within the plurality of devices from the respective data; and, when one or more of the plurality of devices is associated with a normalized rate of change of moisture content that is above a threshold normalized rate of change, provide a notification at a notification device.

Figure 2:
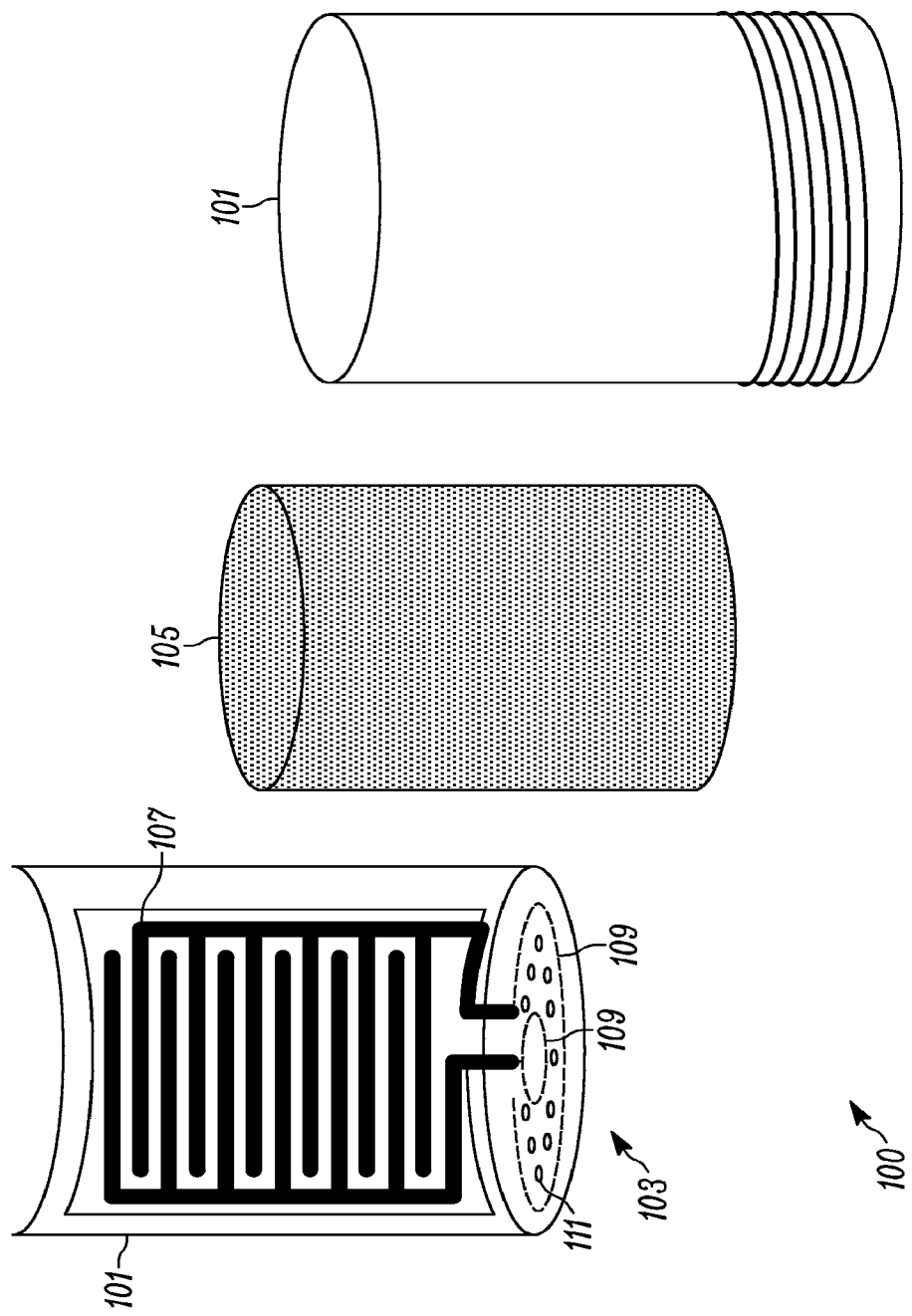
FIG. 2 is an exploded view of the field replaceable desiccant cartridge of FIG. 1, in accordance with some embodiments.

Attention is next directed to FIGS. 1 and 2 which respectively depict a perspective view and an exploded view of a field replaceable desiccant cartridge 100 comprising: a housing 101 comprising an insertion end 103 configured to removabley mate with an aperture of a device (for example see FIGS. 6 to 8, described below), insertion end 103 configured to generally prevent moisture from entering the device when mated; a desiccant 105 located in housing 101; a circuit 107 located within housing 101, circuit 107 in contact with desiccant 105, circuit 107 configured to change resistance as desiccant 105 changes in moisture content; one or more electrodes 109 located at an exterior of insertion end 103, one or more electrodes 109 in contact with circuit 107; and, one or more holes 111 through insertion end 103, configured to expose desiccant 105 to an exterior of housing 101 so that desiccant 105 can absorb moisture there from. One or more holes 111 will be interchangeably referred to hereafter, collectively, as holes 111, and singly as a hole 111. Similarly, one or more electrodes 109 will be interchangeably referred to hereafter, collectively, as electrodes 109, and singly as an electrode 109. Furthermore, while only one hole 111 is numbered in FIGS. 1 and 2, it is appreciated that, in depicted implementations, there is more than one hole; such a numbering convention is adopted for clarity and will be used elsewhere in the present specification. Furthermore, field replaceable desiccant cartridge 100 will be interchangeably referred to hereafter as cartridge 100.

As depicted, insertion end 103 of housing 101 comprises threads 113 configured to screw into corresponding threads of an aperture of a device, in order to create an IP seal and generally prevent moisture from entering the device when mated thereto. While not depicted, insertion end 103 can further comprise any combination of sealing devices, including, but not limited to o-rings, and the like, to assist with such ingress protection when cartridge 100 is mated with the aperture of the device.

Figure 3:
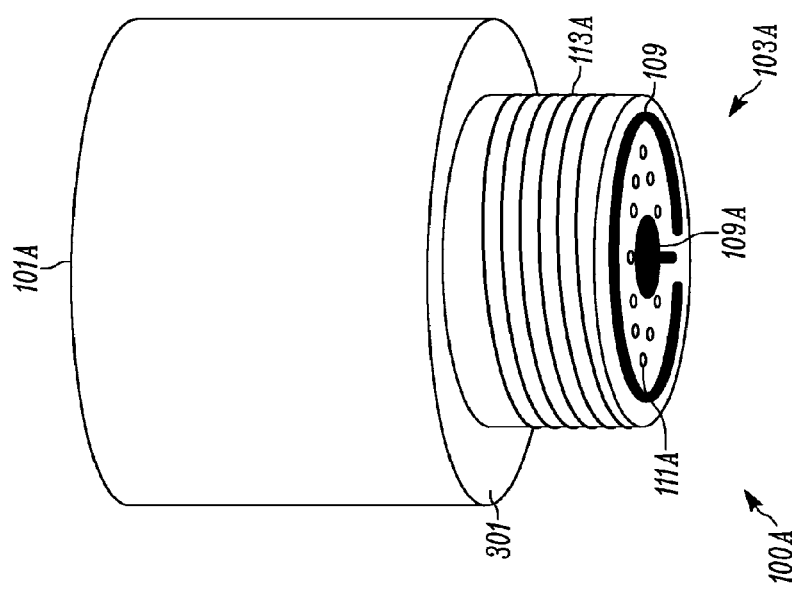
FIG. 3 is a perspective view of an alternative field replaceable desiccant cartridge, in accordance with some embodiments.

As depicted, housing 101 is generally cylindrical, and having the same cylindrical diameter through a longitudinal axis. However, attention is briefly directed to FIG. 3, which an alternative implementations of a cartridge 100a, FIG. 3 being substantially similar to FIG. 1, with like elements having like numbers with an "a" appended thereto; further, while in FIG. 3 an exterior of a housing 101a of cartridge 100a is depicted, from a perspective that also shows electrodes 109a and holes 111a of insertion end 103a, it is assumed that interior components of cartridge 100a are similar to interior components of cartridge 100. In contrast to cartridge 100, insertion end 103a of cartridge 100a is generally cylindrical and of a smaller diameter than a remaining portion of housing 101a, with threads 113a being on a smaller diameter cylinder. Further, while the remaining portion of housing 101a is also cylindrical, the remaining portion can be any shape that can contain a desiccant and a circuit similar to circuit 107. While also not depicted, a face 301 of the remaining portion adjacent insertion end 103a can be configured to seal against a chassis of a device to which cartridge 100a is being mated; for example face 301 can comprise an o-ring and the like.

Returning to FIG. 2, as depicted housing 101 is configured to separate, laterally, into two portions, and further, when housing 101 is assembled, housing 101 forms an IP seal, other than holes 111. However, other configurations of housing 101 are within the scope of present implementations, with housing 101 being generally impermeable to moisture when assembled.

Returning to FIGS. 1 and 2, one or more holes 111 are adjacent one or more electrodes 109, and each of holes 111 and electrodes 109 are located at a cylindrical face of insertion end 103; however, in other implementations, one or more of holes 111 and electrodes 109 can be located at a cylindrical sidewall of insertion end 103.

Figure 4:
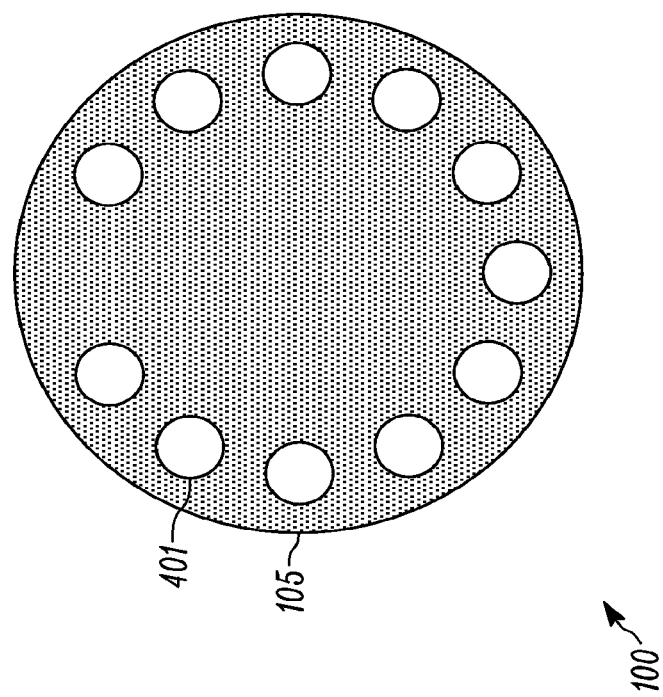
FIG. 4 is an end view of a desiccant of the field replaceable desiccant cartridge of FIG. 1, in accordance with some embodiments.

Desiccant 105 generally comprises a material configured to absorb moisture, including, but not limited to, silica gel, bentonite clay, a molecular sieve, and the like. Housing 101 can be filled with desiccant 105 during manufacture of cartridge 100; hence desiccant 105 can generally assume a shape of housing 101, as depicted in FIG. 2. With reference to FIG. 4, which depicts an end of desiccant 105 which is adjacent holes 111, in some implementations, cartridge 100 further comprises at least one channel 401 in desiccant 105 extending from each of one or more holes 111 into desiccant 105; for example, each channel 401 can be in a one-to-one relationship with holes 111, and each channel 401 can comprise a depression in desiccant 105 to increase exposure of desiccant 105 to ambient atmosphere through each hole 111. Furthermore, while FIG. 4 depicts a channel 401 for each hole 111, in other implementations, there can be fewer channels 401 than holes 111, or fewer holes 111 than channels. Indeed, in some implementations, there are no channels 401 in desiccant 105.

Returning to FIGS. 1 and 2, electrodes 109 are generally connected to circuit 107 through housing 101. Specifically, housing 101 and circuit 107 comprises electrical vias and/or electrical connections through housing 101 and specifically through to electrodes 109. Indeed, in FIG. 2, electrodes 109 are depicted using stippled lines to indicate that electrodes 109 are at an exterior of housing 101 while circuit 107 is at an interior of housing 101, with electrical connections passing through housing 101 to electrically connect them.

Desiccant 105 is generally in contact with circuit 107. For example, with reference to FIG. 2, as depicted, circuit 107 can comprise interdigitated electrodes in contact with desiccant 105; hence, when an ohmmeter circuit, and the like, is in contact with electrodes the resistance between the interdigitated electrodes can be measured. As desiccant 105 is in contact with the interdigitated electrodes of circuit 107, a resistance between the interdigitated electrodes changes as desiccant 105 absorbs moisture. Hence, a resistance between the interdigitated electrodes can be related to moisture content of desiccant 105 and further related to moisture content of a device into which insertion end 103 is inserted.

While circuit 107 is depicted with a specific structure, it is appreciated that any circuit that changes in resistance as a moisture content of desiccant 105 changes is within the scope of present implementations. For example, electrodes of circuit 107 need not be interdigitated. Further, circuit 107 can comprise an electrical component whose resistance changes as the moisture content of desiccant 105 changes, with electrodes 109 connected across such an electrical component.

Similarly, a specific pattern of electrodes 109 is depicted that is compatible and/or complementary with corresponding electrodes in a device with which cartridge 100 is to be mated, as described in further detail below. However, other electrode patterns are within the scope of present implementations.

In some implementations, circuit 107 can comprise a flex circuit. Such a flex circuit can be formed on flexible substrate including, but not limited to, polyamide, and the like. In some of these implementations, electrodes 109 can also be a component of the flex circuit, with a first portion of the flex circuit that includes electrodes 109 being external to housing 101, and a second portion of the flex circuit that includes circuit 107 being internal to housing 101, the two portions being connected through housing 101, for example via an IP sealed slot, and the like; both the first portion and the second portion of circuit 107 can be adhered to housing 101 using, for example, glue, adhesive, heat bonding and the like.

Figure 5:
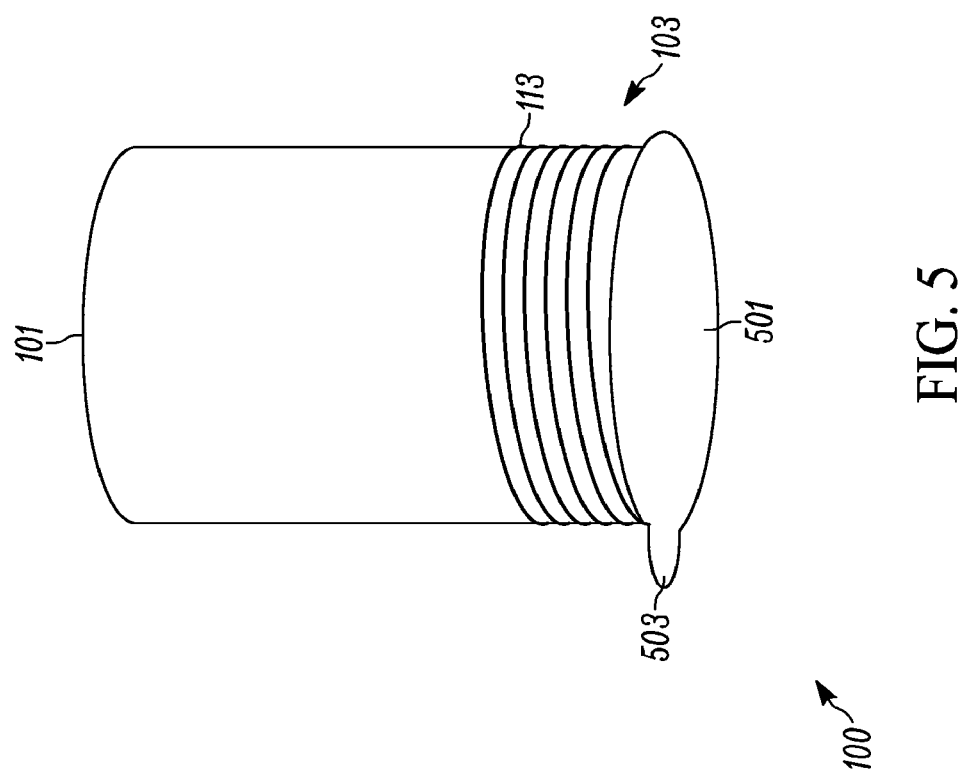
FIG. 5 is a perspective view of the field replaceable desiccant cartridge of FIG. 1 in a shipping configuration, in accordance with some embodiments.

Attention is next directed to FIG. 5 which depicts cartridge 100 in a shipping configuration. Specifically, in these configurations, cartridge 100 further comprises a seal 501 on one or more holes 111 (not visible in FIG. 5 as seal 501 is covering them), seal 501 preventing moisture from entering one or more holes 111. In other words, seal 501 comprises an IP seal of holes 111, seal 501 being applied to cartridge 100 prior to shipping and/or during manufacture, to prevent desiccant 105 from absorbing moisture until mated with an aperture of a device. Seal 501 can hence be one more of removable and punctureable. As depicted, seal 501 comprises a tab 503 which can be gripped in order to peel and/or remove seal 501 from cartridge 100 prior to mating with an aperture of a device; as such seal 501 can comprise a flexible plastic and/or polymer sheet, and the like, which is generally impermeable to moisture, which is attached to insertion end 103, at a time of manufacture and/or prior to shipping, covering holes 111 using one or more of heat sealing, a glue, an adhesive and the like.

Alternatively, respective electrodes within an aperture of a device with which cartridge 100 is to be mated can be configured to puncture seal 501 to allow moisture from inside the device to flow through holes 111, and to allow the respective electrodes of the device to contact electrodes 109. Indeed, as depicted in FIGS. 1 and 2, one or more holes 111 are adjacent one or more electrodes 109 and hence seal 501 further protects one or more electrodes 109, for example against abrasions that might occur during shipping. However, in other implementations, seal 501 can cover holes 111 without covering and/or protecting electrodes 109.

While not depicted, in some implementations, cartridge 100 can further comprise at least one notification device, the notification device configured to provide a notification when the resistance of circuit 107 reaches a threshold resistance. Such a determination of threshold resistance can occur at cartridge 100; in these implementations, cartridge 100 can further comprise a processor, a memory storing the threshold resistance and the notification device, with such components powered by an on-board power source and/or by a device with which cartridge 100 is mated. Alternatively, such a determination of threshold resistance can occur at a processor of a device with which cartridge 100 is mated, and the device processor can cause the notification device to provide the notification; in these implementations, the notification device is powered by the device with which cartridge 100 is mated. Such a notification device can include, but is not limited to, a light, an LED (light emitting diode), a display, an LCD (liquid crystal display), a speaker and the like. Furthermore, cartridge 100 can comprise any suitable number of additional electrodes 109 for powering and/or connecting to and/or controlling and/or interfacing with the notification device and any other associated components; a device with which cartridge is configured to mate can hence comprise complementary electrodes to power and/or connect to and/or control and/or interface with the notification device and any other associated components.

Figure 6:
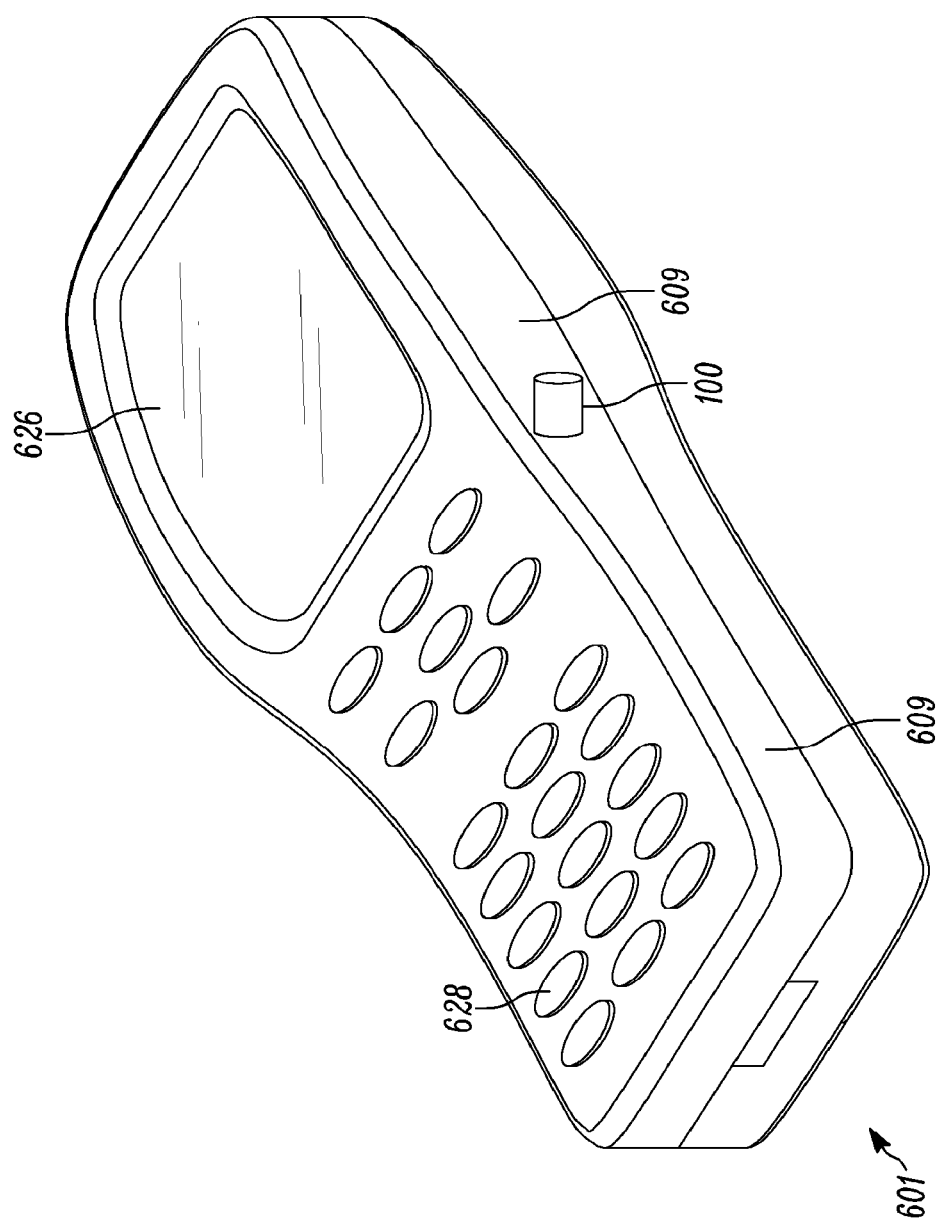
FIG. 6 is a perspective view of a device mated with the field replaceable desiccant cartridge of FIG. 1, in accordance with some embodiments.
Figure 7:
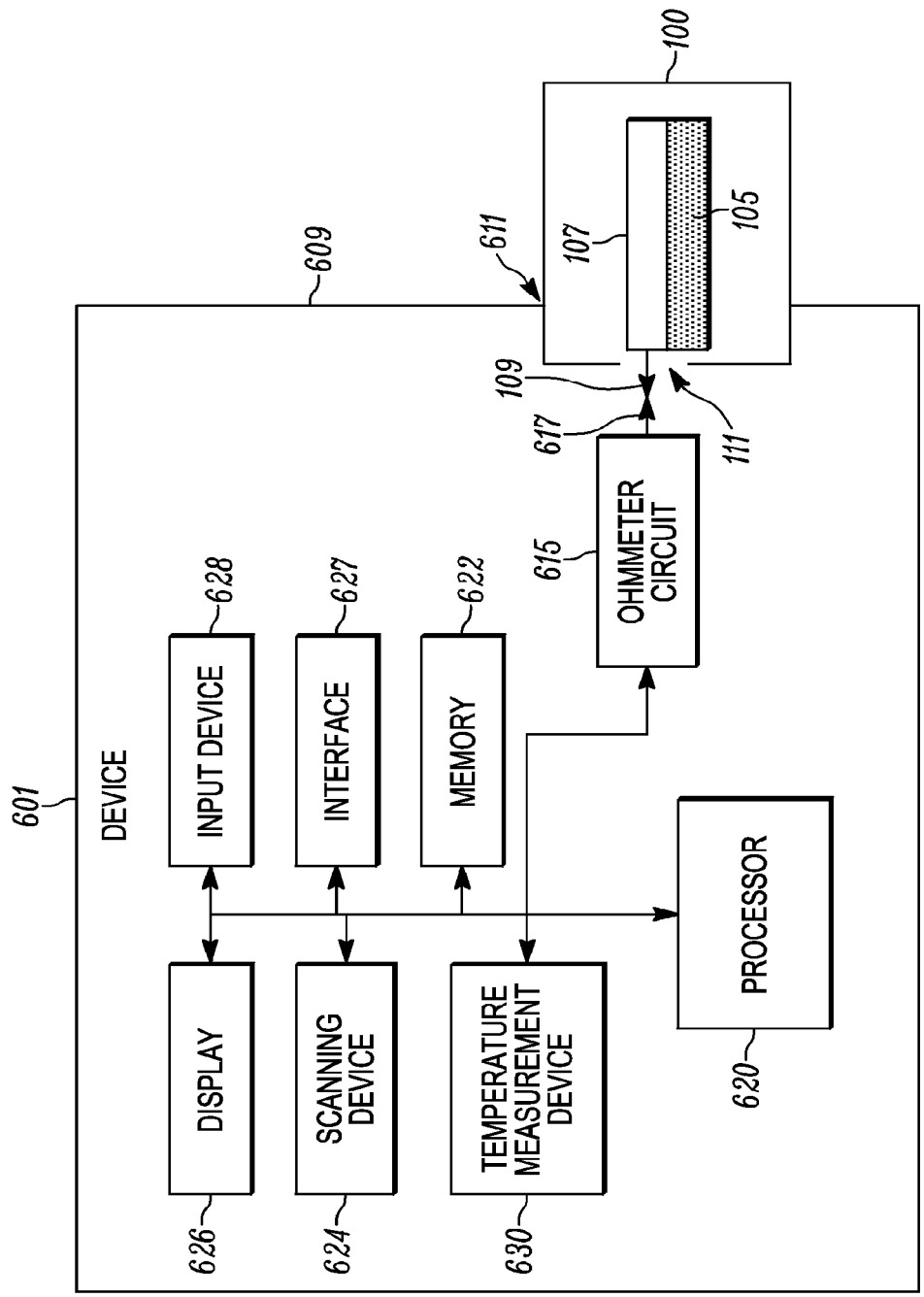
FIG. 7 is a schematic block diagram of the device of FIG. 6, in accordance with some embodiments.

Attention is next directed to FIGS. 6 and 7 which respectively front perspective view and a schematic block diagram of a device 601 with which cartridge 100 can be mated; indeed, as depicted cartridge 100 is mated with device 601. Further, in FIG. 6, only an exterior of cartridge 100 is depicted as extending from device 601 and, in FIG. 7, only desiccant 105, circuit 107, electrodes 109 and holes 111 are schematically depicted, though it is assumed that all components of cartridge 100 are present in both FIGS. 6 and 7.

Anyhow, as depicted, device 601 comprises: a chassis 609 having an aperture 611; a field replaceable desiccant cartridge 100 comprising: housing 101 comprising insertion end 103 configured to removabley mate with aperture 611, insertion end 103 configured to generally prevent moisture from entering device 601 when mated; desiccant 105 located in housing 101; circuit 107 located within housing 101, circuit 107 in contact with desiccant 105, circuit 107 configured to change resistance as desiccant 105 changes in moisture content; one or more electrodes 109 located at an exterior of insertion end 103, one or more electrodes 109 in contact with circuit 107; and, one or more holes 111 through insertion end 103, configured to expose the desiccant 105 to an exterior of housing 101, and an interior of chassis 609 of device 601 when mated thereto, so that desiccant 105 can absorb moisture there from; an ohmmeter circuit 615 configured to measure a resistance of circuit 107 of field replaceable desiccant cartridge 100, ohmmeter circuit 615 comprising one or more respective electrodes 617 configured to contact one or more electrodes 109 of field replaceable desiccant cartridge 100 when mated thereto; and, a processor 620 in communication with ohmmeter circuit 615, processor 620 configured to control ohmmeter circuit 615 to measure the resistance of circuit 107 of field replaceable desiccant cartridge 100.

Device 601 can be any type of electronic device that can be used in a self-contained manner, for example, to gather data. Device 601 can hence include, but is not limited to, any suitable combination of electronic devices, data gathering devices, laptop computers, portable electronic devices, mobile computing devices, portable computing devices, tablet computing devices, laptop computing devices, and the like. Other suitable devices are within the scope of present implementations. However, It should be emphasized that the structure of device 601 in FIG. 1 is purely an example, and contemplates a device that can be used for scanning and/or gathering data, but that other devices are within the scope of present implementations, for example others devices that can be used for specialized functions, including, but not limited, to one or more of, telephony, computing, and the like.

As best seen in FIG. 6, in depicted implementations, chassis 609 can be provided in two parts which, when connected provide an IP seal for an interior of device 601. However, moisture can nonetheless enter device 601 through cracks and/or damage that might occur in chassis 609 and/or other components of device 601 and/or during normal operation of device 601. Indeed, as device 601 is subjected to temperature extremes (for example when device 601 is transported into walk-in refrigerators on hot days and/or transported into heated building interiors on cold days, and vice versa) thermal stress occurs at device 601 which can exacerbate moisture penetration therein. Cartridge 100 can be used to monitor moisture within device 601 as described hereafter.

However, depicted non-limiting implementations of device 601 are first described. With reference to FIGS. 6 and 7, device 601 can further comprise, but is not limited to, at least one input device 628, generally configured to receive input data, and can comprise any suitable combination of input devices, including but not limited to a keyboard, a keypad, a pointing device, a mouse, a track wheel, a trackball, a touchpad, a touch screen and the like. Other suitable input devices are within the scope of present implementations.

Device 601 can further comprise, but is not limited to, a scanning device 624 which can be used to gather data (which can be located at a rear of device 601 and hence is not visible in FIG. 6). For example, scanning device 624 can include, but is not limited, a laser scanning device, a barcode scanner, an optical scanner and the like.

Device 601 can further include, but is not limited to, a display 626 and a communication interface 627. While not depicted, device 601 can further include a power supply, a power store, a battery, and the like. While also not depicted, device 601 can further include a speaker and/or microphone.

Depending on the implementation of the embodiment, the display 626 can be realized as a liquid crystal display (LCD), a touch-sensitive display, a cathode ray tube (CRT), a light emitting diode (LED) display, an organic light emitting diode (OLED) display, a plasma display, a projection display, or another suitable electronic display.

Communication interface 627, which is interchangeably referred to hereafter as interface 627 is configured to exchange data with one or more remote devices using a communication network, and/or receive data from one or more remote devices using a communication network and/or transmit data to one or more remote devices using a communication network. Interface 627 is hence generally configured to communicate with one or more communication networks (for example see FIG. 9) including, but not limited to, wired networks, wireless networks, cell phone networks (including various implementations thereof), WiFi networks, the Internet and the like. Indeed, in particular non-limiting implementations, as depicted, device 601 comprises a portable wireless device and hence interface 627 comprises a wireless communication interface.

Processor 620 runs or executes operating instructions and/or programs, which are stored in memory 622, to perform various functions for the device 601 and to process data. Processor 620 can include one or more microprocessors, microcontrollers, digital signal processors (DSP), state machines, logic circuitry, and/or any device or devices that process information based on operational or programming instructions stored in memory 622. In particular, processor 620 can comprise a hardware processor. Memory 622 can comprise any suitable combination volatile memory and non-volatile memory including, but not limited to random access memory, a hardrive, a flash drive, a solid state drive and the like.

Ohmmeter circuit 615 can comprise one or more of an ohmmeter, a voltmeter, an ammeter, a multimeter and/or any device which can be used to measure, either directly or using intermediate electrical parameters, a resistance of circuit 107. Indeed, measured resistance need not be measured in ohms, but can be measured in any units which can correspond to ohms and/or be proportional to resistance, in either absolute units and/or relative units, including volts and the like; for example, ohmmeter circuit 615 can comprise a digital ohmmeter which measures relative resistance on a scale of 0 to 255, and the like.

As depicted in FIG. 7, device 601 can optionally comprise a temperature measurement device 630. For example, temperature measurement device 630 can comprise a digital thermometer configured to measure one or more of an internal temperature and an external temperature of device 601. Temperature measurement device 630 in generally in communication with processor 620. However, in other implementations, device 601 does not comprise a temperature measurement device 630. Furthermore, while external components of temperature measurement device 630 are not depicted in FIG. 6, when temperature measurement device 630 is configured to measure an external temperature of device 601, such external components can nonetheless be present at chassis 609.

In any event, it should be understood that a wide variety of configurations for device 601 are contemplated.

Furthermore, while a particular location of cartridge 100 relative to chassis 609 of device 601 is depicted in FIG. 6, cartridge 100 (and aperture 611) can be located at any suitable location at chassis 609, for example a location selected using ergonomic principles and the like, and where electrodes 617 can be located inside chassis 609.

In addition, in FIG. 7, aperture 611 is depicted schematically, with aperture 611 being represented by a narrow space between cartridge 100 and chassis 609, however, in general, at least threads 113 and insertion end 103 of cartridge 100 form an IP seal in conjunction with aperture 611.

Figure 8:
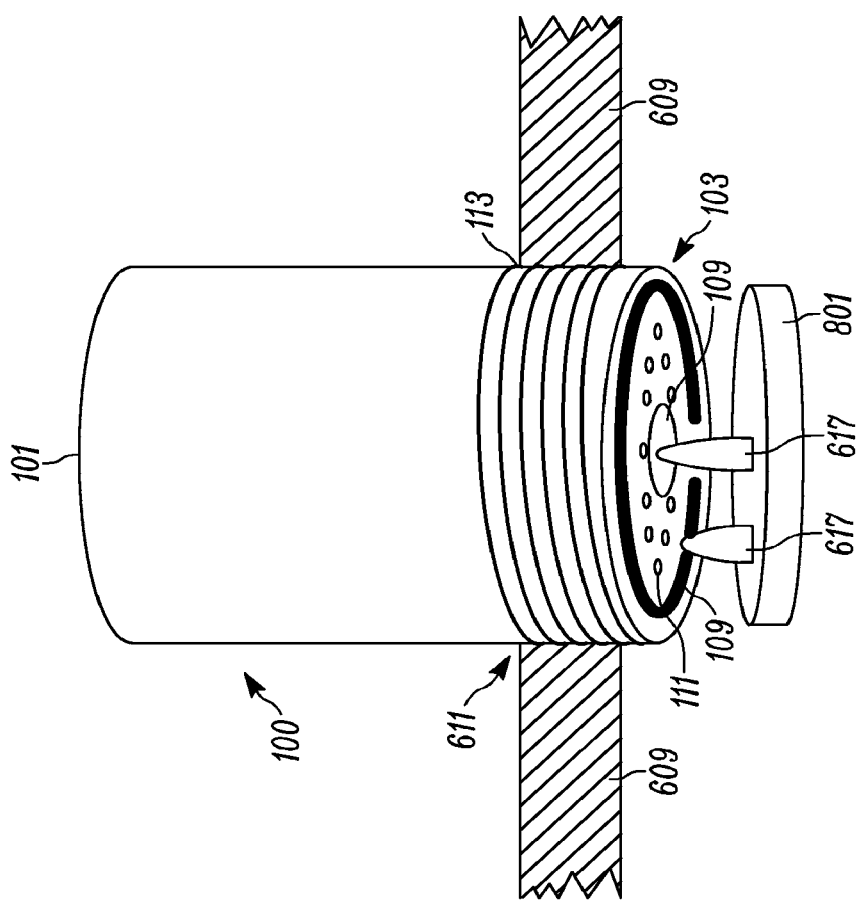
FIG. 8 is a perspective view of the field replaceable desiccant cartridge of FIG. 1, mated with an aperture of the device of FIG. 6, a chassis of the device depicted in cross-section, in accordance with some embodiments.

For example, attention is next directed to FIG. 8 which depicts cartridge 100 mated with aperture 611, with a portion of chassis 609 defining aperture 611 depicted in cross section, as well as non-limiting implementations of electrodes 617, depicted as contacting electrodes 109 in a one-to-one relationship.

In particular, when cartridge 100 is mated with aperture 611, threads 113 mate with complementary threads of aperture 611; colloquially, cartridge 100 can screw into aperture 611, and sidewalls of housing 101 and/or threads 113 form an IP seal with sidewalls and/or threads of aperture 611.

Either of aperture 611 and housing 101 can comprise further sealing devices including, but not limited to, o-rings and the like. However, other mechanisms for removabley mating cartridge 100 with aperture 611 are within the scope of present implementations, including, but not limited to, tabs, fasteners, pressure based fasteners, and the like.

In depicted implementations, device 601 further comprises a cartridge rest 801 against which insertion end 103 can at least partially rest when cartridge 100 is mated with aperture 611. As depicted, cartridge rest 801 comprises a disc of suitable material which is positioned within device 601 at a location which controls a distance that cartridge 100 can be inserted into aperture 611. For example, cartridge 100 can be screwed into aperture until both electrodes 617 contact corresponding electrodes 109, and cartridge rest 801 prevents cartridge 100 from being inserted any further. Alternatively, when device 601 is configured to mate with a cartridge having a configuration of cartridge 100a, a length of insertion end 103a can control the distance into chassis 609 that cartridge 100a is inserted, with electrodes 617 positioned a similar distance within chassis 609. Face 301 can then seal against chassis 609, with an area around aperture 611 configured to seal against face 301.

As such, each of electrodes 617 can comprise a spring electrode, and the like, located at a position corresponding to an electrode pattern of electrodes 109. However, both cartridge rest 801 and electrodes 617 can comprise any suitable shape, configuration, and/or material that provides the described functionality. In addition, while not depicted, each of electrodes 617 is connected to remaining components of ohmmeter circuit 615. In some implementations, electrodes 617 can also be configured to puncture seal 501 when seal 501 is not removable from cartridge 100.

Hence, provided herein is a field replaceable cartridge 100 that can be used instead of a desiccant pack inside device 601, with cartridge 100 being easily removable and replaceable with another cartridge 100 by removing and/or unscrewing a first cartridge 100 from device 601 and replacing it with a second cartridge 100.

In any event, processor 620 is generally configured to control ohmmeter circuit 615 to measure the resistance of circuit 107 of field replaceable desiccant cartridge 100. In some implementations, processor 620 can be further configured to determine when the resistance of circuit 107 reaches a threshold resistance, the threshold resistance being associated with a moisture content of desiccant 105 where device 601 can require servicing, and can be associated with a crack and/or a break in an IP seal. Such a threshold resistance and/or moisture content can be determined heuristically and provisioned at memory 622 at one or more a factory and in a provisioning process. In some implementations, device 601 can comprise a notification device, including, but not limited to, display 626 and/or a speaker, processor 620 can be further configured to provide, at the notification device, a notification to change field replaceable desiccant cartridge 100 when the resistance reaches the threshold resistance. As such, device 601 can be generally configured to provide a notification and/or an alert of when a moisture level within device 601 reaches a level where servicing of device 601 is required; indeed, such a moisture level can be associated with damage to device 601.

Alternatively, processor 620 can be in communication with a notification device of cartridge 100, and control the notification device to provide a notification in addition to, or in alternative to, notifications provided at a notification device of device 601. As such, device 601 can comprise additional electrodes 617 for interfacing with a notification device of cartridge 100.

In yet further implementations, processor 620 can be further configured to control ohmmeter circuit 615 to determine a rate of change of the resistance by measuring the resistance periodically. Presuming device 601 and/or processor 620 includes a clock device, a rate of change of resistance can be determined, which can be associated with a rate of change of the moisture level within device 601; when the rate of change is above a threshold rate of change, processor 620 can again cause a notification device to provide a notification thereof. For example, a rate of change that is above a threshold rate of change can be associated with damage to device 601, such as a crack and/or a break in an IP seal, such that moisture content within device 601 is increasing faster than without a crack and/or a break in an IP seal.

In yet further implementations, as described in further detail below, processor 620 can be further configured to transmit, using interface 627, one or more of the resistance and a rate of change of the resistance to a server. Furthermore, when device 601 comprises temperature measurement device 630, processor 620 can be further configured to transmit, using interface 627, one or more of a temperature of device 601 and a record of temperatures of device 601, and an indication of a transition between a warm environment and a cold environment, along with one or more of the resistance and the rate of change of the resistance to a server. For example, memory 622 can store a threshold temperature difference and when a temperature of device 601 changes by more than the threshold temperature difference over a given time period, processor 620 can determine that a transition between a warm environment and a cold environment has occurred and store an indication thereof. For example, when a temperature of device 601 changes by more than about 10° C. over about 5 minutes, processor 620 can store an indication of a transition between a warm environment and a cold environment at memory 622, though other thresholds are within the scope of present implementations and can be determined heuristically.

Figure 9:
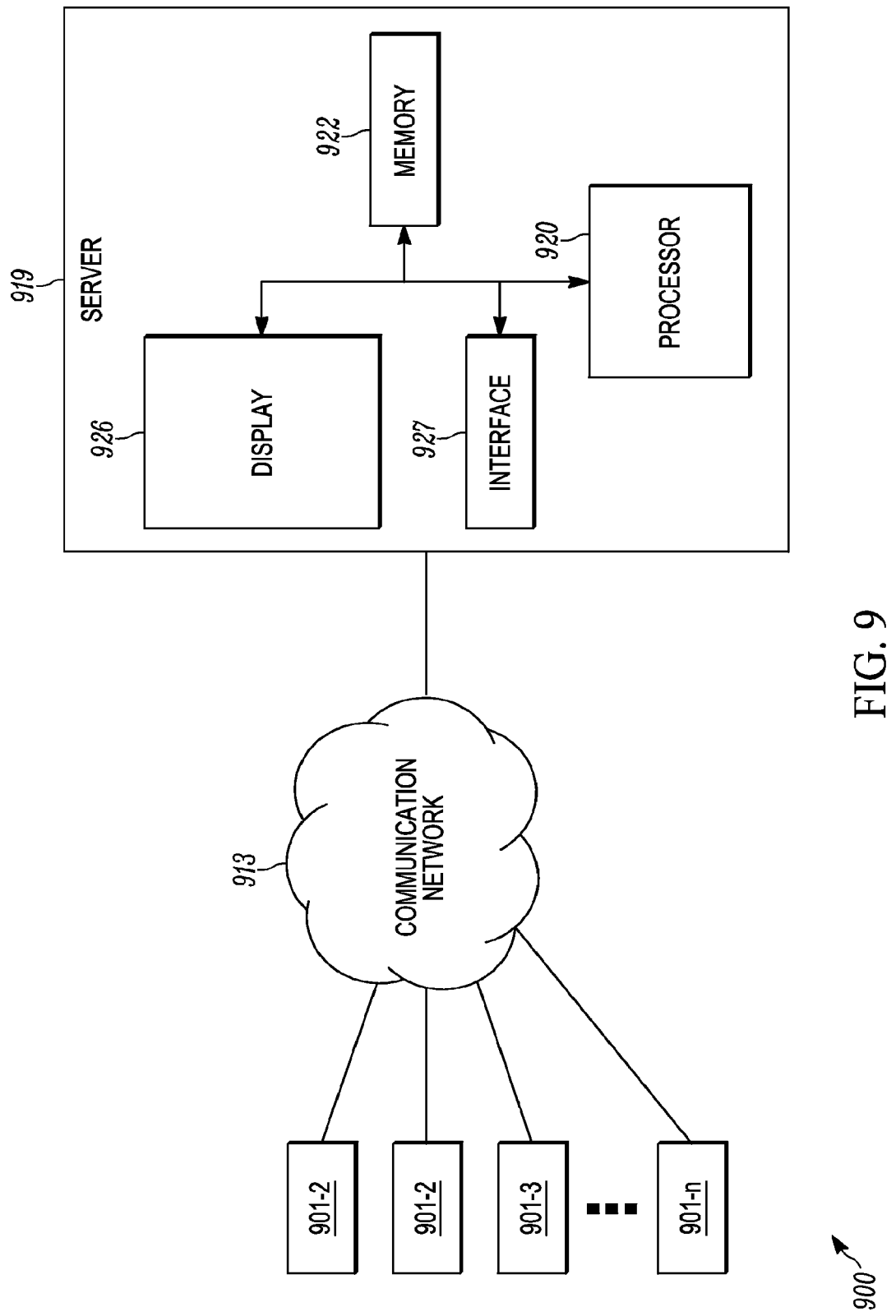
FIG. 9 depicts a system for determining when devices configured with the field replaceable desiccant cartridge of FIG. 1 need servicing, in accordance with some embodiments.

Attention is next directed to FIG. 9 which depicts a system 900 comprising a plurality of devices 901-1, 901-2, 901-3 . . . 901-n, each substantially similar to device 601 and each comprising a respective field replaceable desiccant cartridge (not depicted). Devices 901-1, 901-2, 901-3 . . . 901-n will be interchangeably referred to hereafter, collectively, as devices 901 and generically as a device 901. System 900 further comprises at least one communication network 913 (interchangeably referred to hereafter as network 913), compatible within respective communication interfaces of devices 901, and a server 919. Each of devices 901 and server 919 is in communication with network 913 via a respective wired and/or wireless link, represented in FIG. 9 by lines between each component and network 913.

Server 919 comprises: a processor 920 and a communication interface 927, each respectively similar to processor 620 and interface 627, though each of processor 920 and interface 927 can be adapted for server functions rather than handheld device functions. As depicted, server 919 further comprises a memory 922 and a display 926, and each can be respectively substantially similar to memory 622 and display 626, though adapted for server functions. While not depicted, server 919 can further comprise one or more input devices and the like.

As will be described in further detail below, server 919 is generally configured to communicate with each of devices 901, and further manage devices 901. For example system 900 can comprise a system of handheld scanners (e.g. devices 901) which are deployed by an entity that is also managing server 919 and server 919 can be used to determine when service is to occur for each of the handheld scanners, though other types of devices are within the scope of present implementations and techniques described herein can also be applied to devices other than handheld scanner. While system 900 is depicted with four devices 901, in other implementations, system 900 can comprise as few as one device 901 and as many as hundreds to thousands of devices 901. Furthermore, functionality of server 919 can be embodied in more than one server.

For example, processor 920 is generally configured to: receive, using the communication interface 927, from plurality of devices 901, respective data indicating moisture content in a respective desiccant cartridge of each of plurality of devices 901, and one or more indications of respective transitions between a warm environment and a cold environment, as described above; determine respective indications of normalized rates of change of moisture content within plurality of devices 901 from the respective data; and, when one or more of plurality of devices 901 is associated with a normalized rate of change of moisture content that is above a threshold normalized rate of change, provide a notification at a notification device. Such notification device can include display 926, a notification device at one or more of plurality of devices 901 and a notification device at another computing device, for example a computing device associated with service personnel.

Indeed, in some implementations, processor 920 can be further configured to: transmit, using communication interface 927, to one or more of the plurality of devices 901 associated with the normalized rate of change of moisture content that is above the threshold normalized rate of change, an alert to have a respective device 901 serviced. Alternatively, a notification device comprises display 926, and a notification that a normalized rate of change of moisture content that is above a threshold normalized rate of change comprises a visual notification at display 926.

Figure 10:
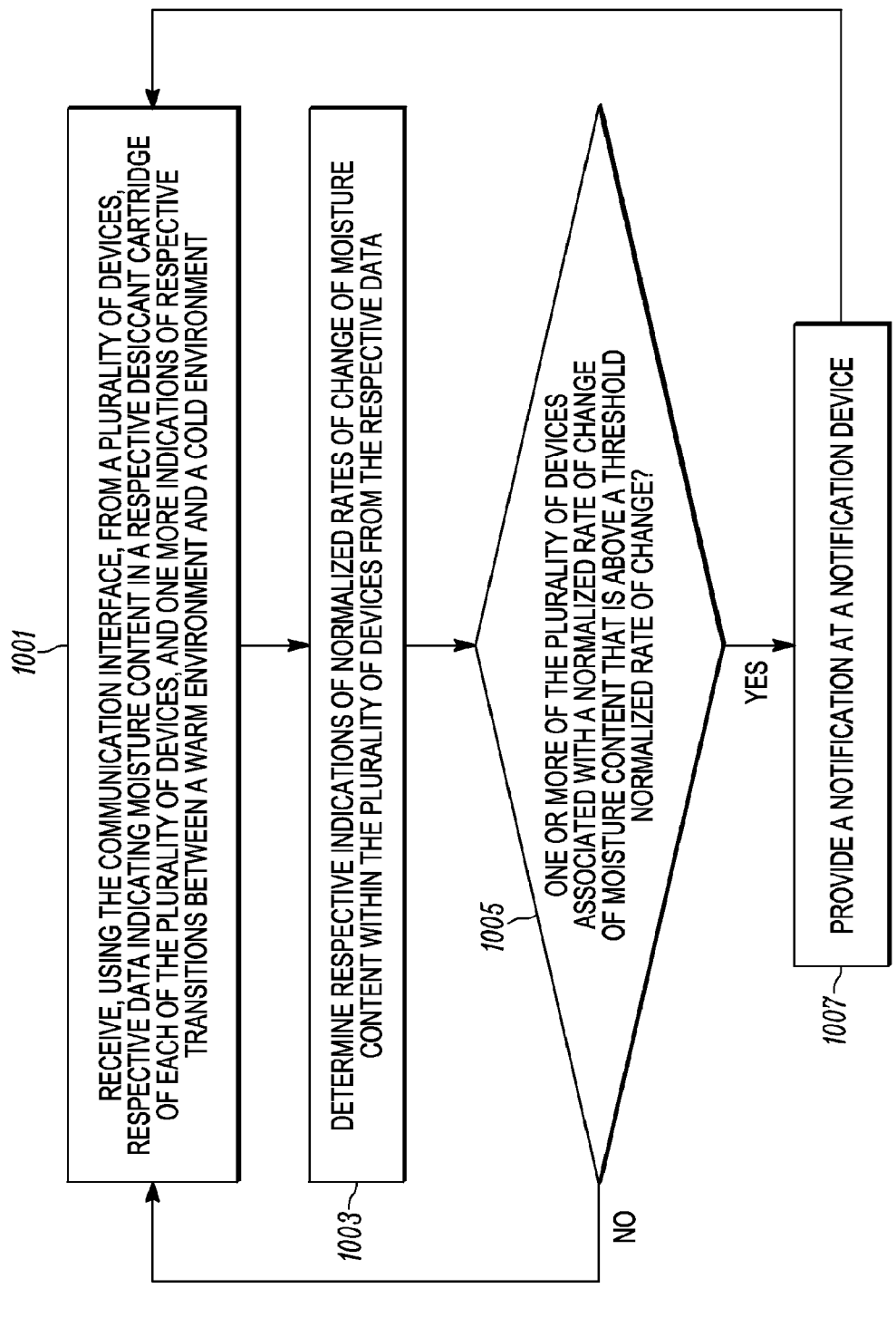
FIG. 10 depicts a method of determining when devices configured with the field replaceable desiccant cartridge of FIG. 1 need servicing, in accordance with some embodiments.

Attention is now directed to FIG. 10 which depicts a flowchart of a method 1000 for managing devices 901, according to non-limiting implementations. In order to assist in the explanation of method 1000, it will be assumed that method 1000 is performed using server 919, and specifically by processor 920 of server 919. Indeed, method 1000 is one way in which server 919 can be configured. Furthermore, the following discussion of method 1000 will lead to a further understanding of server 919, and its various components. However, it is to be understood that server 919 and/or method 1000 can be varied, and need not work exactly as discussed herein in conjunction with each other, and that such variations are within the scope of present implementations.

Regardless, it is to be emphasized, that method 1000 need not be performed in the exact sequence as shown, unless otherwise indicated; and likewise various blocks may be performed in parallel rather than in sequence; hence the elements of method 1000 are referred to herein as "blocks" rather than "steps". It is also to be understood, however, that method 1000 can be implemented on variations of system 100 as well.

At block 1001, using interface 927, processor 620 receives from plurality of devices 901, respective data indicating moisture content in a respective desiccant cartridge of each of plurality of devices 901, and one more indications of respective transitions between a warm environment and a cold environment.

At block 1003, processor 620 determines respective indications of normalized rates of change of moisture content within the plurality of devices from the respective data received at block 1001.

At block 1005, processor 620 determines whether one or more of the plurality of devices is associated with a normalized rate of change of moisture content that is above a threshold normalized rate of change, for example as stored at memory 922.

When one or more of the plurality of devices is not associated with a normalized rate of change of moisture content that is above a threshold normalized rate of change (i.e. a "NO" decision at block 1005), block 1001 is again implemented.

However, when one or more of the plurality of devices is associated with a normalized rate of change of moisture content that is above a threshold normalized rate of change (i.e. a "YES" decision at block 1005), at block 1007, processor 620 provides a notification at a notification device.

Method 1000 will now be described with reference to FIGS. 11 to 13, with FIGS. 11 and 13 being substantially similar to FIG. 9, with like elements having like numbers.

Figure 11:
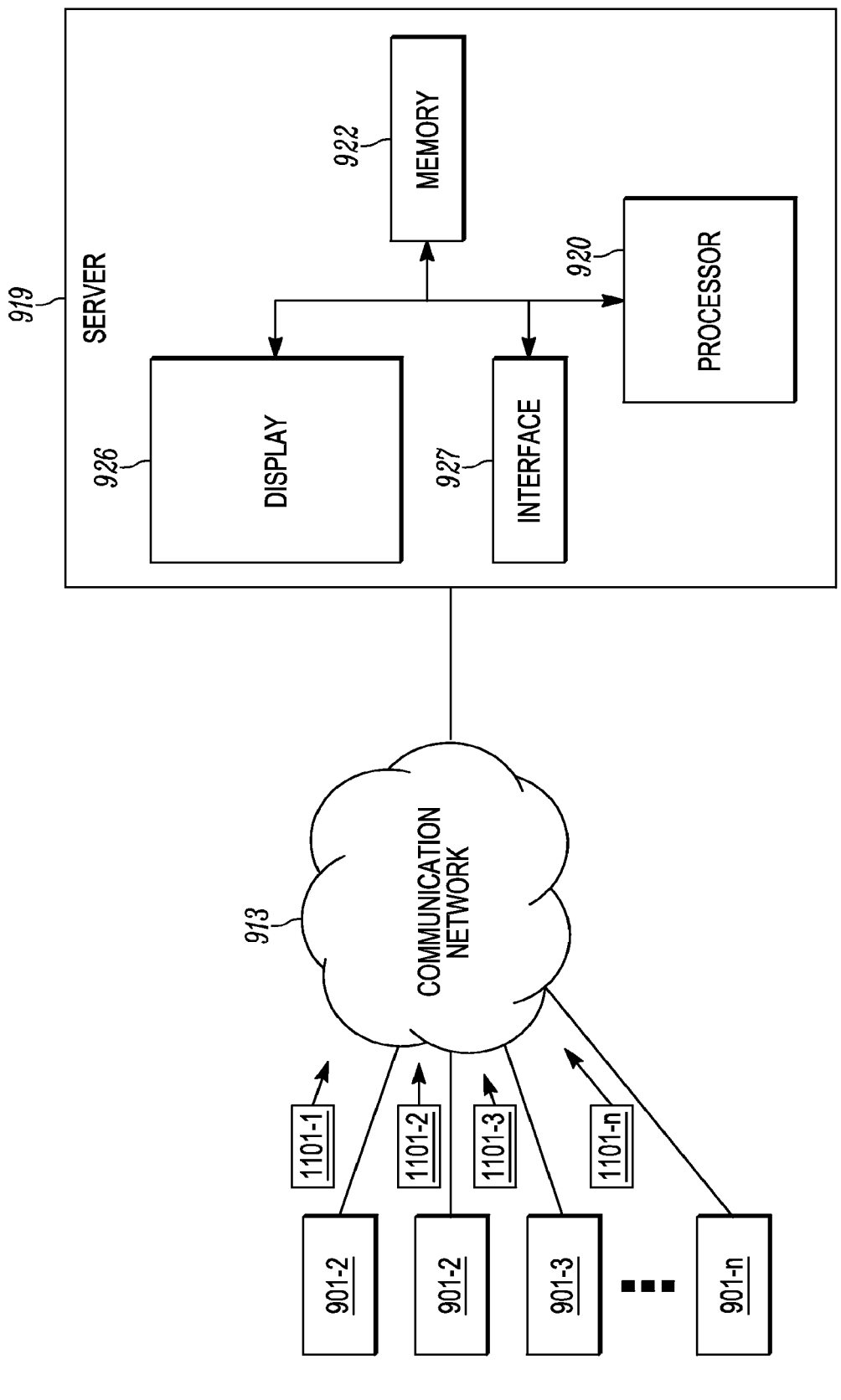
FIG. 11 depicts the system of FIG. 9 with devices transmitting moisture content and temperature data to a server, in accordance with some embodiments.

In FIG. 11, each of devices 901 transmit respective data 1101-1, 1101-2, 1101-3 . . . 1101-n, which is interchangeably referred to hereafter, collectively, as data 1101 and generically as data 1101. Data 1101 can be respectively transmitted periodically and/or when a transition between a warm environment and a cold environment is detected at respective device 901 as described above. Data 1101 is received at server 919 (block 1001). Data 1101 can comprise respective data indicating moisture content in a respective desiccant cartridge of each of plurality of devices 901, and one more indications of respective transitions between a warm environment and a cold environment of each of devices 901, as well as a respective identifier of a device 901.

Processor 620 determines respective indications of normalized rates of change of moisture content within the plurality of devices 901 from data 1101 (block 1003). For example, attention is directed to FIG. 12, which depicts a visual representation of such normalized rates of change of moisture content for each of devices 901, though processor 620 does not necessarily calculate or provide such a visual representation; rather such a visual representation is provided for clarity only, and to better describe present implementations.

Figure 12:
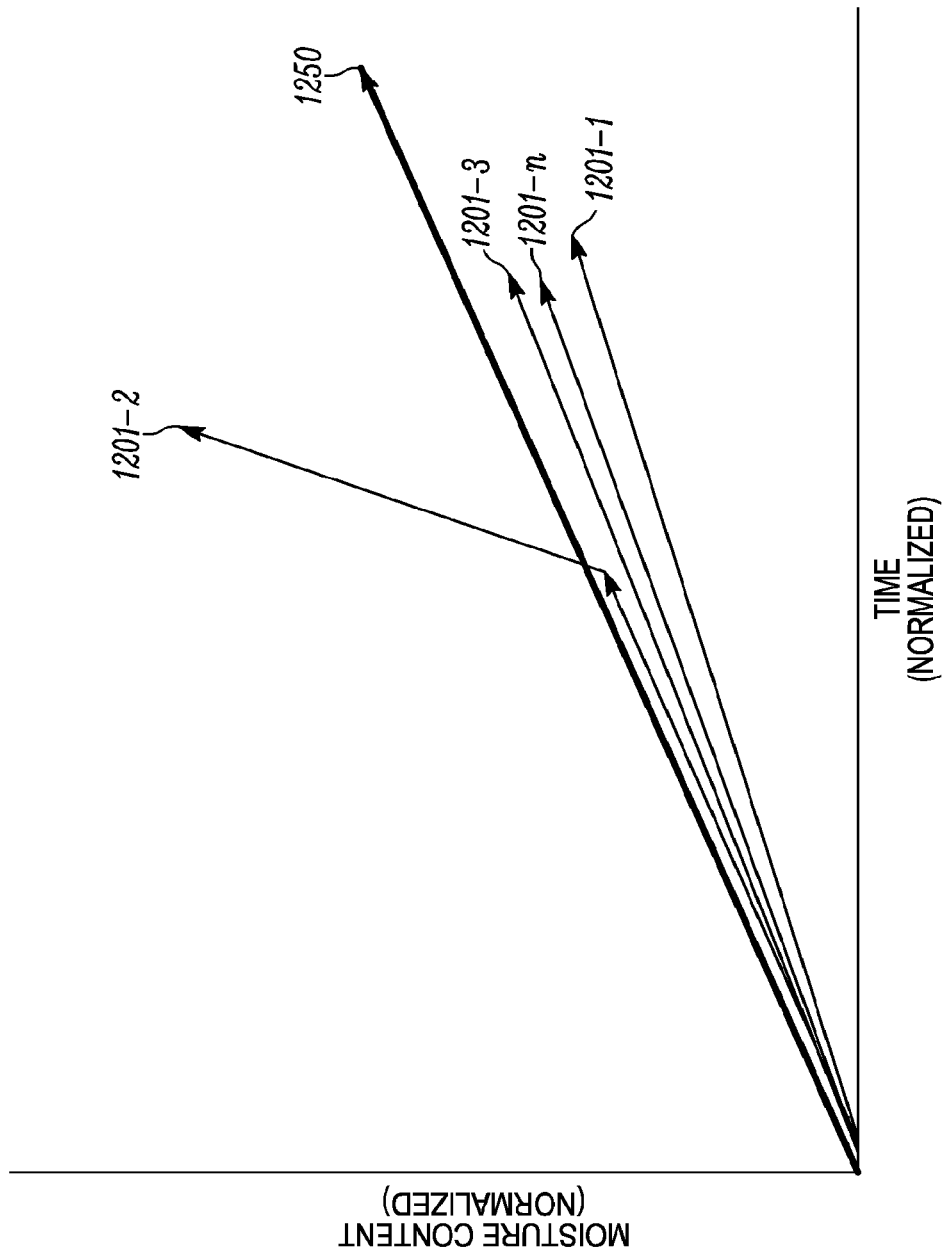
FIG. 12 depicts normalized rates of change of moisture content of devices in the system of FIG. 9, in accordance with some embodiments.

Specifically, FIG. 12 depicts curves 1201-1, 1201-2, 1201-3 . . . 1201-n of normalized moisture content vs. normalized time for each of devices 901, with curve 1201-1 associated with device 901-1, curve 1201-2 associated with device 901-2, curve 1201-3 associated with device 901-3 and curve 1201-n associated with device 901-n. Curves 1201-1, 1201-2, 1201-3 . . . 1201-n will be interchangeably referred to hereafter collectively as curves 1201 and generically as a curve 1201. In any event, each curve 1201 has been normalized, for example, based on a number of transitions between a warm environment and a cold environment for each respective device 901. Any suitable normalization scheme can be used to produce curves 1201 from data 1101, including, but not limited to, determining un-normalized rate of change and dividing through by a respective number of transitions between a warm environment and a cold environment for each respective device 901.

Also depicted in FIG. 12 is a threshold normalized rate of change 1250, also graphically depicted. It is apparent that each of curves 1201-1, 1201-3, 1201-n are below threshold normalized rate of change 1250, but curve 1201-2 undergoes a abrupt change and rises rapidly above threshold rate of change 1250, which can be associated with damage to an IP seal of device 901-2. Hence, at block 1005, can use calculations that correspond to the visual representations of curves 1201 to determine whether one or more of plurality of devices 901 is associated with a normalized rate of change of moisture content that is above a threshold normalized rate of change 1250. Prior to the abrupt change, a "NO" decision occurs at block 1005, however after the abrupt change, a "YES" decision occurs at block 1005 as processor 920 determines that device 901-2 is associated with a normalized rate of change 1201-2 of moisture content that is above a threshold normalized rate of change 1250.

Figure 13:
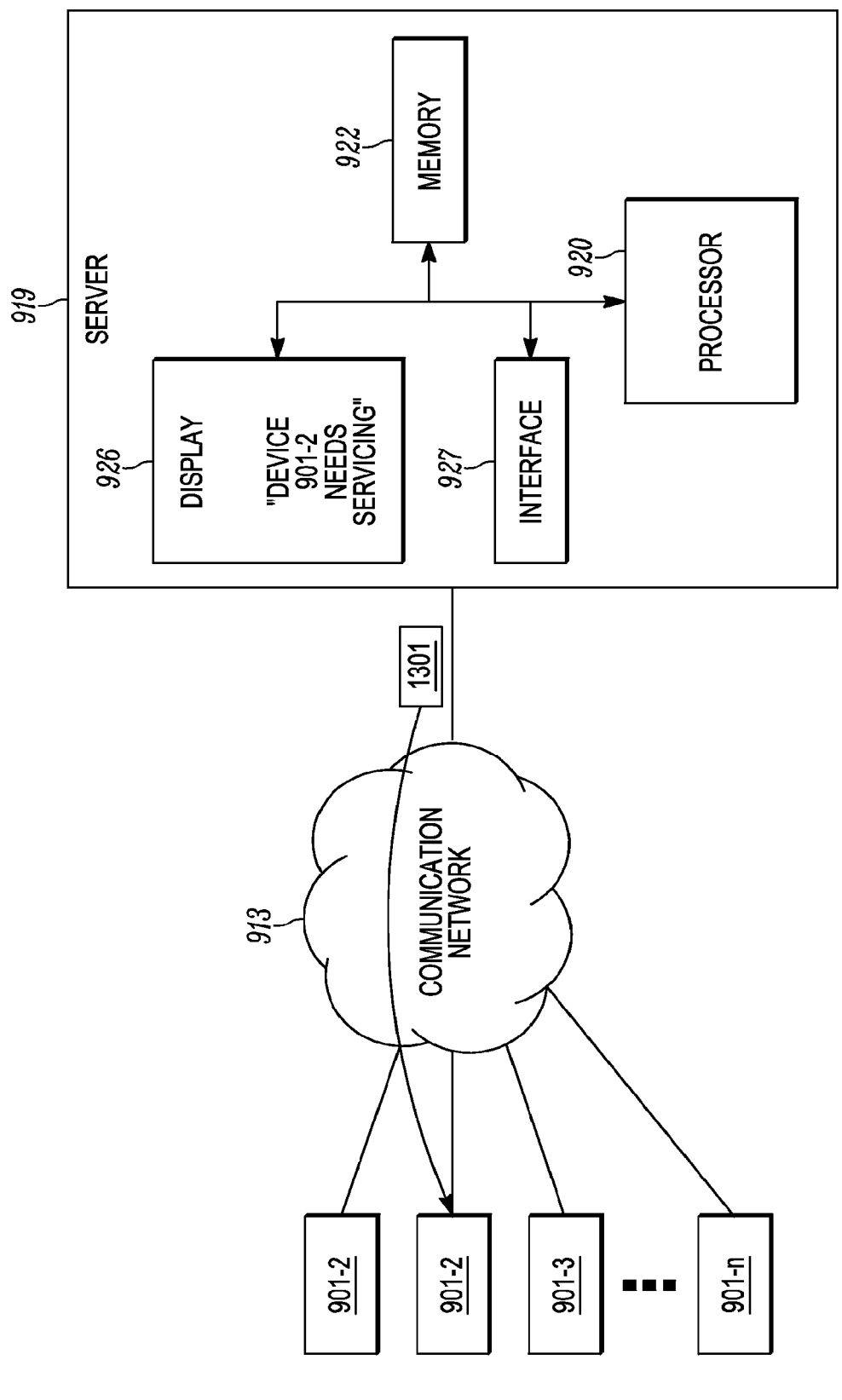
FIG. 13 depicts the system of FIG. 9 with the server providing notifications of service, in accordance with some embodiments.

As such, and with reference to FIG. 13, processor 620 can control display 926 to provide a notification ("Device 901-2 needs servicing") and/or transmit an alert 1301 of such to device 901-2 using network 913 and/or transmit an alert to computing device (not depicted) associated with service personnel (block 1007). When alert 1301 is received at device 901-2, and/or an alert is received at the computing device associated with service personnel, device 901-2 and/or the computing device associated with service personnel can provide a respective indication at a respective display that device 901-2 is to be services, retrieved for service and/or brought in for service.

In some implementations, threshold normalized rate of change 1250 can be determined from an average of curves 1201; hence, threshold normalized rate of change 1250 can represent an average of the moisture content behavior of devices 901, and when one device 901-2 deviates from the population, device 901-2 is flagged for service.

Hence, implementations described herein provide a system in which data from a population of handheld terminals, and the like, is periodically analyzed by a server, and when one or more of the handheld terminals indicates that the level of moisture is increasing faster than the average of the population of handheld terminals, the server can determine that it is highly likely that the IP seal of that handheld terminal is compromised, indicating that the handheld terminal should be serviced. The accuracy of the analysis can be further increased by normalizing the increase in moisture relative to the number of transitions between a warm and cold environment. The transitions between warm and cold environments can be detected by a temperature sensor on the handheld terminal, and the data from the temperature sensor can also be collected by processors of respective handheld terminals and forwarded to the server for analysis.

Furthermore, determination of moisture content at each of the handheld terminals can occur via a field replaceable cartridge at each handheld terminal that includes a circuit in contact with a desiccant, the circuit changing resistance as the desiccant absorbs moisture from within a handheld terminal.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A server comprising:
a processor and a communication interface; the processor configured to:
receive, using the communication interface, from a plurality of devices, respective data indicating moisture content in a respective desiccant cartridge of each of the plurality of devices, and one more indications of respective transitions between a warm environment and a cold environment;
determine respective indications of normalized rates of change of moisture content within the plurality of devices from the respective data; and,
when one or more of the plurality of devices is associated with a normalized rate of change of moisture content that is above a threshold normalized rate of change, provide a notification at a notification device.

2. The server of claim 1, wherein the processor is further configured to: transmit, using the communication interface, to the one or more of the plurality of devices associated with the normalized rate of change of moisture content that is above the threshold normalized rate of change, an alert to have a respective device serviced.

3. The server of claim 1, wherein the notification device comprises a display, and the notification comprises a visual notification at the display.

* * * * *